United States Patent [19]

Haschke et al.

[11] 4,058,662

[45] * Nov. 15, 1977

[54] PROCESS FOR THE SUBSTITUTION OF CHLORINE ATOMS OF CYANURIC CHLORIDE

[75] Inventors: Heinz Haschke, Weissenstein ob der Drau, Austria; Gerd Schreyer, Hanau, Germany; Werner Schwarze, Frankfurt, Germany; Helmut Suchsland, Rodenbach, Germany

[73] Assignee: Deutsche Gold- und Silber-Scheideanstalt Vormals Roessler, Frankfurt, Germany

[ * ] Notice: The portion of the term of this patent subsequent to Oct. 18, 1994, has been disclaimed.

[21] Appl. No.: 656,849

[22] Filed: Feb. 10, 1976

[30] Foreign Application Priority Data

Feb. 12, 1975 Germany .............................. 2505704

[51] Int. Cl.² ............................................ C07D 251/50
[52] U.S. Cl. .................................... 544/208; 544/204
[58] Field of Search ............................ 260/249.5, 249.8

[56] References Cited

U.S. PATENT DOCUMENTS

| | | | |
|---|---|---|---|
| 3,244,712 | 4/1966 | Knusli et al. ................. | 260/249.5 X |
| 3,505,325 | 4/1970 | Schwarze et al. ................ | 260/249.8 |
| 3,590,040 | 6/1971 | Ferguson et al. ................. | 260/249.5 |
| 3,766,182 | 10/1973 | Kuhne et al. ..................... | 260/249.8 |
| 3,821,220 | 6/1974 | Daugherty et al. ............... | 260/249.8 |
| 3,947,374 | 3/1976 | Lottelman et al. ............... | 260/249.5 |

FOREIGN PATENT DOCUMENTS 1,964,619  4/1973  Germany .......................... 260/249.5

*Primary Examiner*—John M. Ford
*Attorney, Agent, or Firm*—Cushman, Darby & Cushman

[57] ABSTRACT

Figure 1:
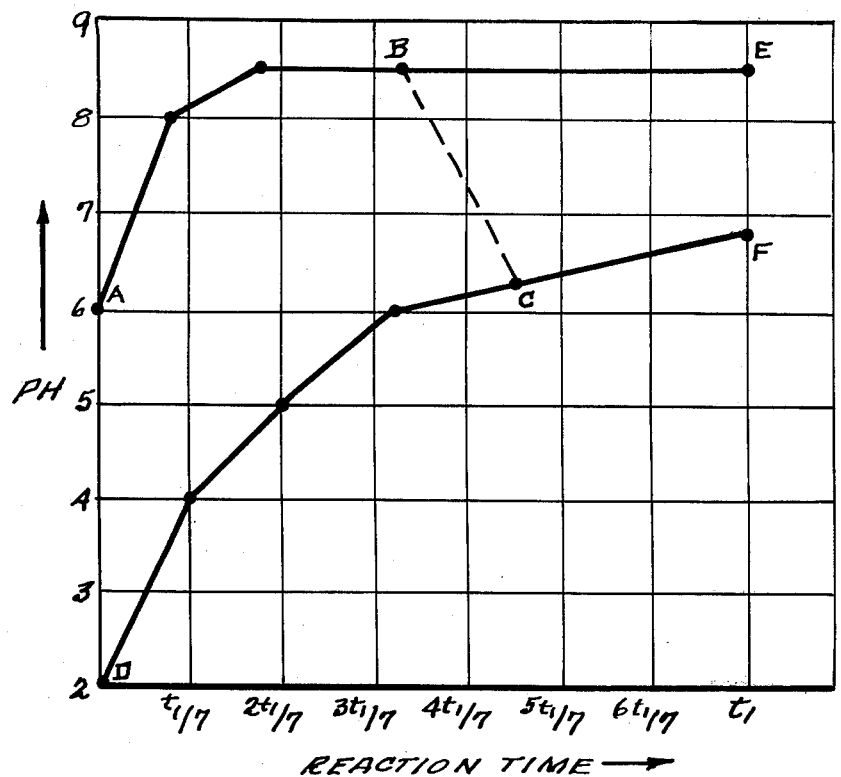
Figure 3:
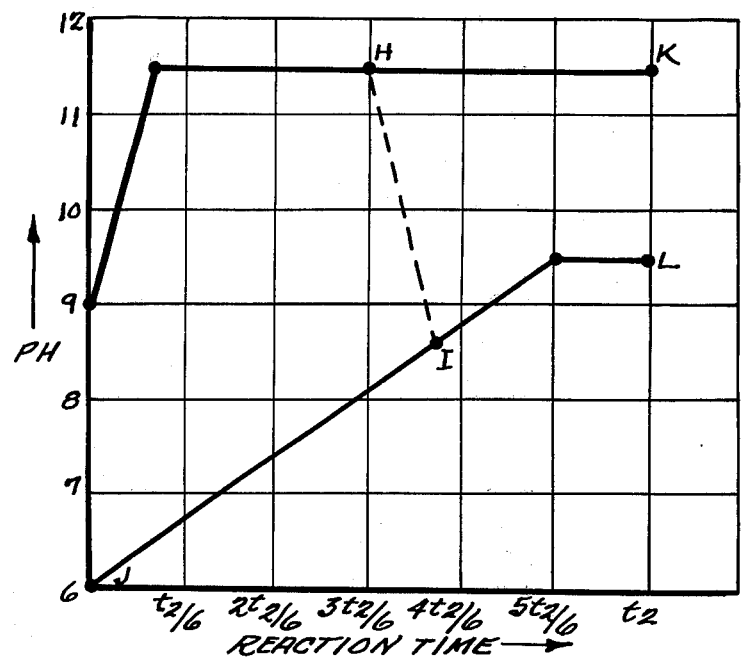

There is provided a process, preferably continuous and in a given case successive, substitution of one or two chlorine atoms of cyanuric chloride by one or two amines, which may be the same or different, in the presence of an acid acceptor and in the presence of an organic solvent, particularly for the production of 2-alkylamino-4,6-dichloro and preferably for the production of 2,4-di(alkylamino)-6-chloro-s-triazines wherein there is added 1.00 to 1.05 mole, preferably 1.00 to 1.03 mole of a first amine to a 4.5 to 50 weight % suspension or solution of cyanuric chloride in a mixture of 65 to 85 weight % of xylene, toluene, ethylbenzene, benzene and/or an aliphatic or cycloaliphatic hydrocarbon with 5 to 10 carbon atoms (toluene being preferred) and 35 to 15 weight % of a ketone with 3 to 8 carbon atoms, preferably acetone, while maintaining the temperature between about 0 and about 20° C, preferably about 10 to 18° C., continuously so regulating the pH value of the reaction mixture obtained in accordance with the reaction time by addition of alkali and in a given case, water so that this corresponds to a point within the area bounded by lines ABCD of FIG. 1, which runs through the area beginning with the reaction time $t_1$(step 1)= 0 until reaching a position in the area bounded by the lines BCEF and after reaching a pH of 7.0, preferably 7.2 maintains a temperature of about 10° to about 60° C., preferably about 25° to 40° C., after addition of 0.96 to 1.05, preferably 0.98 to 1.02 equivalents of alkali per mole of cyanuric chloride, adding at least an equimolar amount, preferably 1.00 to 1.02 mole of the second amine per mole of cyanuric chloride and continuously so adjusting the pH value of the reaction mixture obtained depending on the reaction time by addition of alkali that this corresponds to a point within the area which is defined by lines GHIJ in FIG. 3 which passes through the band beginning with the reaction time $t$(step 2)= 0 of the second reaction step until reaching a position in the area bounded by the lines HIKL and thereby maintaining a temperature of 40 to 70° C., preferably 45° to 55° C. and thereafter working up the product in known manner wherein $t_1$ is a time of 4 to 10 hours, preferably about 7 hours and $t_2$ is a time of 2 to 8 hours, preferably about 6 hours and wherein the B C corresponds to the equation, pH = $-(12.6/t_1) + 14.35$ and the line H I corresponds to the equation pH = $-(24,857/t_2) + 23.9285$. There are also disclosed novel, purified mono and bis alkylamino-cyanoalkylalkylamino — s — triazines.

21 Claims, 5 Drawing Figures

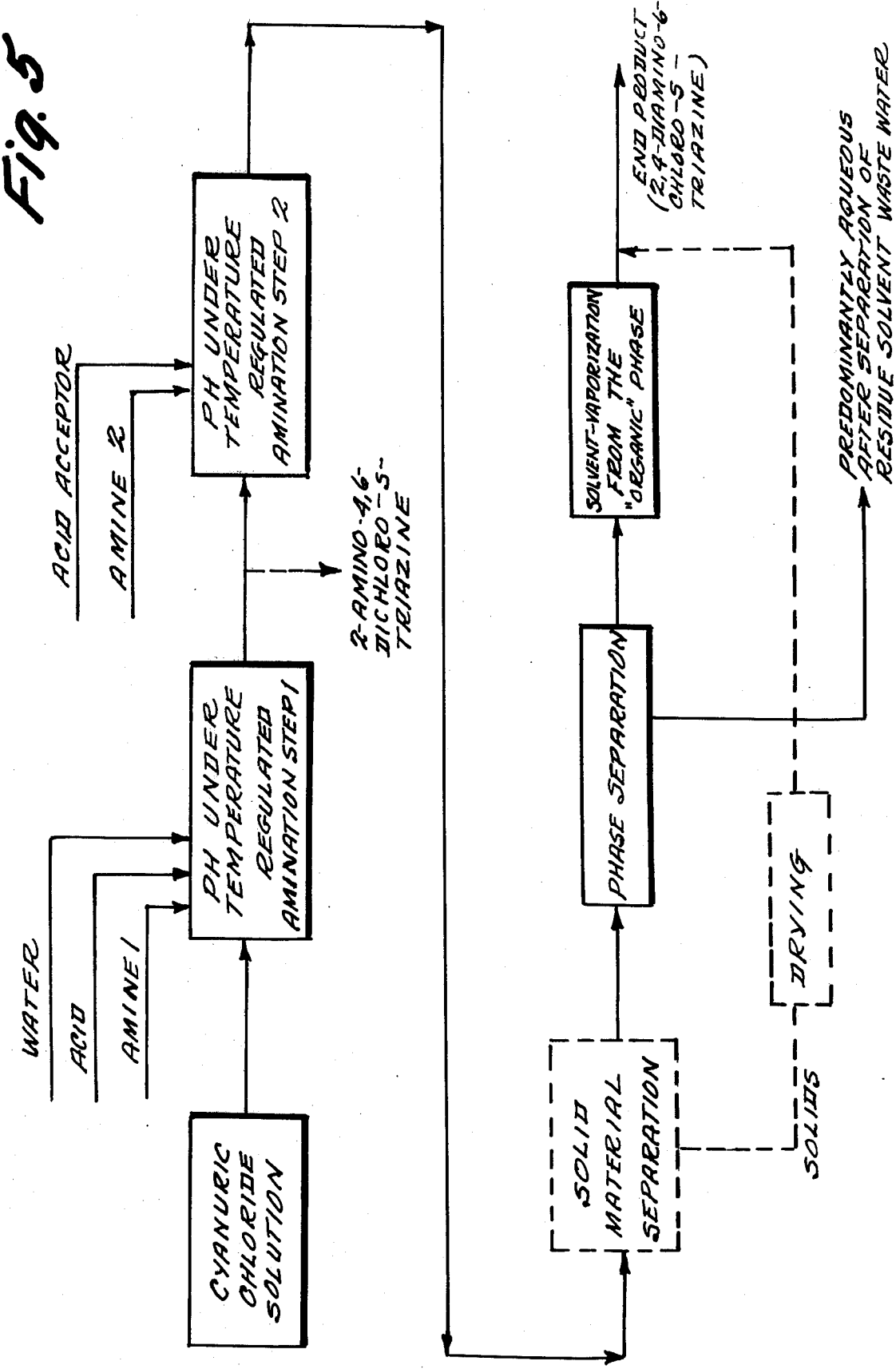

PROCESS FOR THE SUBSTITUTION OF CHLORINE ATOMS OF CYANURIC CHLORIDE

The object of the invention is to develop a process for the substitution of one, or more preferably, two chlorine atoms in cyanuric chloride for the production of 2-alkylamino-4,6-dichloro or preferably 2,4-bis-dialkylamino-6-chloro-s-triazines in very high yields and of remarkable purity. The alkyl group or groups can be substituted as pointed out hereinafter.

It is known to produce these types of compounds by successive reaction of cyanuric chloride with two amines which may be the same or different (i.e. the amine in the first step can be the same or different from that in the second step) in the presence of an acid acceptor and a solvent. As acid acceptor there can be used for example alkalis, especially sodium hydroxide, and as solvent for example toluene, benzene, carbon tetrachloride or the like, see Ferguson U.S. Pat. No. 3,590,040. The entire disclosure of said United States patent is hereby incorporated by reference and relied upon. In the use of these solvents the reaction takes place with the first amine only relatively slowly, so that in the second step of the reaction the second amine can react with still unreacted cyanuric chloride. This is especially the case when a cyanoalkyl amine is the reacting amine. The result of this effect is in each case a lower yield and, especially if the reactions with two different amines occur in succession, considerable byproduct formation. For example, according to the conventional processes yields of 2-isopropylamino-4-ethyl-amino-6-chloro-s-triazine cannot exceed about 95% of theory, whereby in spite of this relatively low yields highly impure end products are obtained through the presence of byproducts, i.e. particularly by 2,4-bis-ethylamino -or 2,4-bis-isopropylamino-6-chloro-s-triazine, e.g. Ferguson U.S. Pat. No. 3,590,040 and Ferguson German Offenlegungsschrift 1,645,948. The entire disclosures of Ferguson U.S. Pat. No. 3,590,040 and German O.G. 1,645,948 are hereby incorporated by reference and relied upon. Besides it is also known to use ketones as solvents for the reaction of cyanuric chloride with amines. if the reactions of cyanuric chloride with amines, for example, are carried out in acetone or in acetone/water systems according to Schwarze German Pat. No. 1,670,541 and related Schwarze U.S. Pat. No. 3,505,325 likewise there is only attainable a maximum yield of about 95%; in the production of 2-cyanoalkylamino-4-alkylamino-6-chloro-s-triazines the maximum attainable yields are only about 93% of theory. The entire disclosures of Schwarze German Pat. No. 1,670,541 and Schwarze U.S. Pat. No. 3,505,325 are hereby incorporated by reference and relied upon. In carrying out the corresponding synthesis reactions in such ketones which are only partially miscible with water, as is described in German Auslegeschrift 1,695,177 (the entire disclosure of which is hereby incorporated by reference and relied upon) the maximum attainable yields of 2,4-dialkylamino-6-chloro-s-triazines with dissimilar amines is only about 97.5%. For example, in the production of 2-isopropylamino-4-ethylamino-6-chloro-s-triazine the yield is 97.5% with a product purity of 99.6%. In the synthesis of cyanoalkyl amino-amino-chloro triazines the yields are substantially poorer. All of these processes besides have the following disadvantages: since a combination of the reactants takes place which is only slightly controlled timewise and therewith scarcely considering the kinetics of the reaction, byproducts, which on occasion can be taken up in considerable measure, particularly with two quick additions of acid acceptor, practically cannot be avoided and therewith clear reduction in yields. Therefore, there have been attempts to produce a certain advance by a calculated or semi-empirically ascertained optimal carrying out of the reaction, for example using fixed time variable reactant deficiencies or excesses depending on the actual analytical results of the end or intermediate products (see Smith U.S. Pat. No. 3,712,976) or by controlling through the heat of reaction developed (compare Tandon German Offenlegungsschrift 1,964,619 the entire disclosure of which is hereby incorporated by reference and relied upon) or carrying out the reaction adiabatically by the additional further cyanuric chloride after the second chlorine atom has been replaced with an alkylamino group (see Petree U.S. Pat. No. 3,681,337 the entire disclosure of which is hereby incorporated by reference and relied upon), or by immediate reduction in the pH after substantial reaction in order to avoid too great increase of undesired, alkali catalyzed side reactions (as, for example, the hydrolysis of the chlorotriazine) see Saul, U.S. Pat. No. 3,681,335, the entire disclosure of which is hereby incorporated by reference and relied upon, or by selection of certain mild acid acceptors such as ammonia in place of alkali hydroxide (see Saul German Offenlegungschrift 1,670,042 and related Saul U.S. Pat. No. 3,436,394, the entire disclosures of the Saul German O.S. and Saul U.S. patent being hereby incorporated by reference and relied upon). In all previously known processes there cannot be avoided a not inconsiderable portion of completely or partially unreacted products or of byproduct formation. It has been ascertained that to obtain higher reactions there must also be maintained higher acid acceptor (alkali) concentrations in the reaction mixture (see Ferguson, U.S. Pat. No. 3,590,040) whereby, however, necessarily the byproduct formation, only through the alkali catalyzed chlorotriazine hydrolysis (see H. Zollinger et al., Helv. Chem. Acta, Vol. 54, 1 (1971) No. 14, pages 163-183) correspondingly increases (see Saul German OG 1,670,042). This problem, however, could not be solved by the use of milder acid acceptors such as ammonia (see Saul German OG 1,670,042) because the $NH_3$ molecule is so nucleophilic that it competes with the desired amines as reactants with the cyanuric chloride or 2-amino-4,6-dichloro-s-triazines with the formation of a simple aminochloro-triazine byproducts. Therefore, there is additional expense caused by keeping low the danger of aminochlorotriazine formation (see A. W. Hofmann, Ber. 18 (1885) pages 2755 to 2776, H. E. Fierz-David et al, J. Soc. Dyers and Colourists 63 (1937), pages 424 et seq.; Hechenbleikner U.S. Pat. No. 2,476,546). Special difficulties result based on principle in the production of cyanoalkylamino-chloro-s-triazines since the cyanoalkylamine necessary therefor, which actually only are amino forms of cyanohydrins, always are inclined under the conditions of the cyanuric chloride substitution, both in the presence of alkali and water as well as of the H Cl set free in the reaction, to split back into the corresponding cyanohydrins and ammonia, which necessarily results in the loss of yield and the formation of aminochlorotriazines as byproducts. Consequently previously according to the known state of the art with no process can there be produced a yield of more than 93 to 94% of theory in the synthesis of cyanoalkylamino(alkylamino)-chloro-s-triazines (see Schwarze U.S. Pat. No. 3,505,325, Schwarze German patent 1,670,541, and U.S. Pat. No. 3,234,225, the entire disclosure of these patents is hereby incorporated by reference and relied upon).

It has now been found that the above-named disadvantages can be avoided in the preferably continuous and in a given case successive, substitution of one or two chlorine atoms of cyanuric chloride by one or two amines, which may be the same or different, in the presence of an acid acceptor and in the presence of an organic solvent, particularly for the production of 2-alkylamino-4,6-dichloro and more preferably for the production of 2,4-di-(alkylamino)-6-chloro-s-triazines (or appropriate substituted alkylamino-chloro-s-triazines) wherein there is added 1.00 to 1.05 mole, preferably 1.00 to 1.03 mole of a first amine to a 4.5 to 50 weight % suspension or solution of cyanuric chloride in a mixture of 65 to 85 weight % of xylene, toluene, ethylbenzene, benzene and/or an aliphatic or cycloaliphatic hydrocarbon with 5 to 10 carbon atoms (toluene being preferred) and 35 to 15 weight % of a ketone with 3 to 8 carbon atoms, preferably acetone, while maintaining the temperature between about 0 and about 20° C., preferably about 10° to 18° C., continuously so regulating the pH value of the reaction mixture obtained in accordance with the reaction time by addition of alkali and in a given case water so that this corresponds to a point within the area bounded by lines ABCD of FIG. 1, which runs through the area beginning with the reaction time $t$, (step 1) = 0 until reaching a position in the area bounded by the lines BCEF and after reaching a pH of 7.0, preferably 7.2 maintains a temperature of about 10° to about 60° C., preferably about 25° to 40° C., after addition of 0.96 to 1.05, preferably 0.98 to 1.02 equivalents of alkali per mole of cyanuric chloride, adding at least an equimolar amount, preferably 1.00 to 1.02 mole of the second amine per mole of cyanuric chloride and continuously so adjusting the pH value of the reaction mixture obtained depending on the reaction time by addition of alkali that this corresponds to a point within the area which is defined by lines GHIJ in FIG. 3 which passes through the band beginning with the reaction time $t$(step 2) = 0 of the second reaction step until reaching a position in the area bounded by the lines HIKL and thereby maintaining a temperature of 40° to 70° C., preferably 45° to 55° C. and thereafter working up the product in known manner wherein $t_1$ is a time of 4 to 10 hours, preferably about 7 hours and $t_2$ is a time of 2 to 8 hours, preferably about 6 hours and wherein the line BC corresponds to the equation pH = $-(12.6/t_1) + 14.35$ and the line HI corresponds to the equation pH = $-(24,857/t_2) + 23.9285$. There are also provided mono and bis alkylamino cyanoalkylalkylamino — s — triazines of unusually high purity as to be novel per se.

Particularly good and constant results are produced in the continuous carrying out of the process, which procedure is advantageous because of the favorable space — time — yields producible thereby. Thereby there are suitably used cyanuric chloride solutions or suspensions in a concentration which is dependent on the ketone content of the organic reaction mixture employed as follows:

Weight % of cyanuric chloride = 0.2 times the weight % of ketone in the solvent mixture plus 1.5 up to K, where K is the number 15, or more preferably 5. It is particularly advantageous in the continuous process to use solutions of cyanuric chloride.

As solvent mixtures there can be used with particular advantages those composed of (a) 65 to 75 weight % of one or more hydrocarbons of the group of aliphatic hydrocarbons having 5 to 10 carbon atoms, namely pentane, hexane, heptane, octane, nonane and decane and/or their isomers, e.g. isodecane, 2-ethylhexane, isooctane, or 3,3-dimethylpentane, as well as cyclohexane and/or aromatic hydrocarbons, namely benzene, toluene, ethyl benzene or xylene (o, m, or p, or mixtures thereof) and (b) 35 to 25 weight % of one or more ketones with 3 to 8 carbon atoms, e.g. aliphatic or cycloaliphatic ketones including dialkyl ketones and cyclo-alkyl ketones such as acetone, methyl ethyl ketone, diethyl ketone, methyl n-propyl ketone, methyl isopropyl ketone, methyl n-butyl ketone, methyl isobutyl ketone, ethyl n-amyl ketone, ethyl isoamyl ketone, ethyl n-hexyl ketone, cyclohexanone or cyclopentanone.

In the synthesis of cyanoalkylamino chlorotriazines it is particularly favorable to use as the solvent a mixture of about 70 weight % toluene and about 30 weight % of a ketone which corresponds to the cyanoalkylamine used, i.e. would produce this in the reaction with HCN and $NH_3$. Acetone has proven to be particularly advantageous as the ketone component.

Particularly high purities are produced if there is so undertaken the timewise regulation of the pH value in the reaction mixture that after addition of the first amine the reaction mixture with maintenance of a temperature between about 0 and about 20° C., preferably about 10° to about 18° C., is subjected to the following conditions successively through addition of alkali and, in a given case, water.

1a. pH 3.5 to 5, preferably 4.25 to 4.75 during an average residence time of 3 to 43, preferably 9 to 21 minutes;

1b. pH 4.5 to 6.25, preferably 5.0 to 5.5 during an average residence time of 0 to 56, preferably 3 to 18 minutes;

1c. pH 5.5 to 7.0, preferably 5.75 to 6.25 during an average residence time of 17 to 189, preferably 51 to 93 minutes;

1d. pH 7.0 to 8.0, preferably 7.25 to 7.90, during an average residence time of 30 to 493, preferably 135 to 330 minutes, whereby simultaneously there is maintained a temperature of 10° to 50° C., preferably of 15° to 35° C. and whereby steps (1a) and (1b) can be combined into a single step and steps (1b) and (1c) can be combined into a single step and that in the case of the synthesis of 2,4-di(alkylamino)-6-chloro-s-triazines (or the corresponding substituted alkylamino compounds) after addition of the second amine the reaction mixture with maintenance of a temperature between about 40 and about 70° C., preferably about 45° to about 55° C., is subjected to the following conditions successively through addition of alkali.

2a. pH 6.5 to 8.0, preferably 6.75 to 7.25, during an average residence time of 2 to 60, preferably 10 to 30 minutes;

2b. pH 7.25 to 9.00, preferably 7.5 to 8.0, during an average residence time of 0 to 92, preferably 0 to 36 minutes;

2c. pH 8.0 to 10.0, preferably 8.25 to 8.75, during an average residence time of 0 to 172, preferably 9 to 66 minutes;

2d. pH 10.0 to 11.75, preferably 10.25 to 10.75, during an average residence time of 15 to 408, preferably 135 to 306 minutes, and wherein steps (2a) and (2b) can be combined into a single step and steps (2b) and (2c) can also be combined into a single step, and that the reaction mixture obtained is worked up in known manner.

Figure 2:
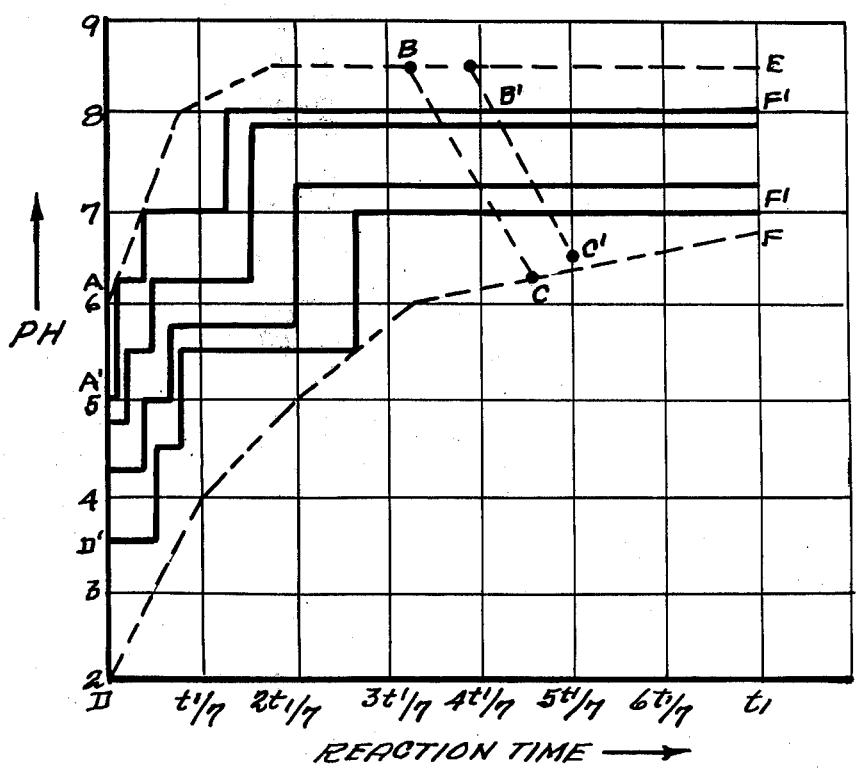
Figure 4:
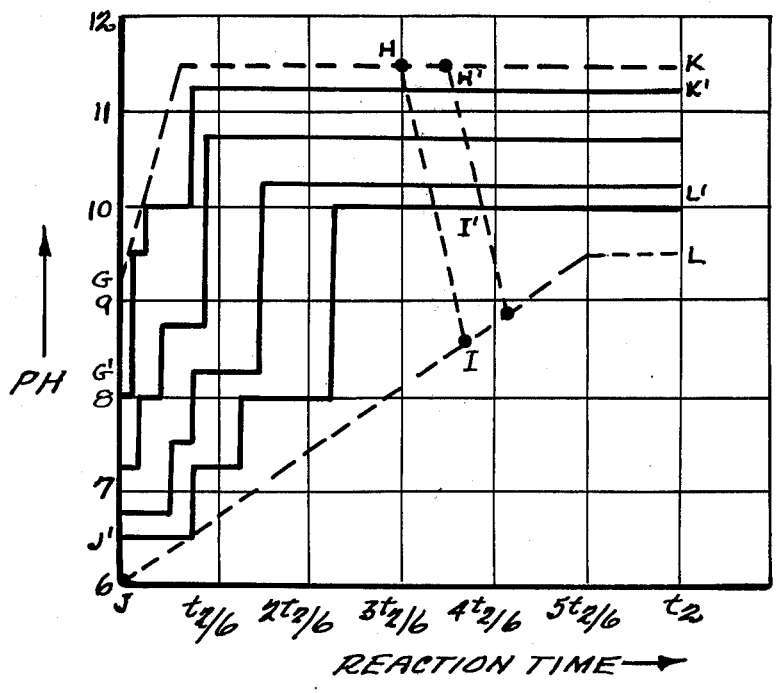

The lines or areas in the pH-time-diagram for the preferred timewise pH regulation are set forth graphically in FIGS. 2 and 4 of the drawings. If the individual reaction steps instead of being broken off at the lines BC or HI are broken off shortly thereafter at the lines parallel thereto B'C' or H'', there are obtained especially high yields. The line B'C' is defined that it goes through the point C' which corresponds to the equation pH = 7.0; $t = (19/28)t_1$ the line H'I' is defined that it goes through the point H' which corresponds to the equation pH = 11.25; $t = (71/120)t_2$. It is understood that on the basis of obtaining the highest possible space-time-yields not to be meaningful to extend the reaction times substantially beyond the lower limits given by the lines B C or B'C' and HI or H'I', although it is possible to go beyond these limits to a certain extent. In the drawing out of the post reaction times too long, i.e. somewhat beyond the lines E F or E'F' and/or beyond the lines K L or K'L' (FIGS. 3 and 4), there must be considered the reduction in the purity of the product because of side reactions, especially hydrolytic side reactions. However, the above reaction time limit naturally is not very sharp. From the information of the individual points, a particularly favorable running of the process is characterized by as discrete steps (1a) to (1d) or (2a) to (2d) the precise process segments resulting in the step-like lines ("ribbons") or areas in the pH-time-diagram. A corresponding stepwise pH-time-progress can be simply realized both in the discontinuous (batchwise) process variant and also in the continuous procedure if there is established in the batch process timewise in succession, in the continuous process flow corresponding to the average residence time of the product stream in individual zones, for example the reactors of a cascade of reactors, spatially in succession by corresponding addition of acid acceptor, about horizontally corresponding pH values inside the lines or areas in the pH-time-diagram. However, naturally there can also take place a fewer step-like or generally steady timewise regulation of pH, assuming that a line is kept inside the corresponding ribbon or area. Individual, short interval stepping above or below the line disadvantageously affects both the yield produced and the purity of the product. It is estimated that the loss of yield of pure product which arises by faulty alkali alkali dosing which causes stepping over the line is about proportional to the area under the indentation which shows as pH-time progress beyond the line or area. For example, if a stepping over a line by about one pH unit lasts only several seconds, there is not effected a very strong reduction in yield of pure product; however, if such a stepping over of the line lasts several minutes there must immediately be reckoned with a loss of pure product to 95% and below.

The data in connection with the process of the invention for establishing the pH values is produced by the so-called electrometrical pH measurement by means of a glass electrode ( = single rod — measuring cell of the firm Schott and Gen., Jena: H63, Abl. Thalamid, Type H, Zero point pH = 7, platinum diaphragm), which was calibrated in pure aqueous buffer solution at 20° C. before the measurement and then was directly inserted into the reaction mixture without temperature and medium effect correction. Thereby the pH value data mentioned produced a purely empirical specific acidity measurement for the given measuring arrangement. They are thus acidity comparisons with the aqueous buffer solutions used for the standardization, namely buffer pH = 7; phosphate buffer and buffer pH = 9; boric acid — KCl — NaOH.

It is advantageous if before or shortly after the beginning of the addition of the acid acceptor there is added to the reaction mixture a certain amount of water, i.e. about 0.5 to 25 weight % based on the amount of solvent, with the introduction of the first amine, for example a cyanoalkyl amine so that there is established a hydrocarbon — ketone — water system composition containing 99.5 to 80 weight % hydrocarbon — ketone mixture and 0.5 to 20 weight % water. It is particularly favorable to add so much water to the reaction mixture in the first reaction step before the beginning of the addition of the acid acceptor that there is found a hydrocarbon — ketone — water mixture of the composition 99.5 to 98.0 weight % hydrocarbon — ketone — mixture and 0.5 to 2 weight % water and the balance of the water, i.e. to a hydrocarbon — ketone — water mixture composition of 95 to 80 weight %, preferably of 88 to 84 weight %, hydrocarbon — ketone mixture and 5 to 20 weight %, preferably 12 to 16 weight % water, is first added when there is reached in the reaction mixture a pH value of at least 4.5, preferably at least 5.0, thus at the beginning of step (1b).

Independent of the named addition of water before or at the beginning of the dosing of the acid acceptor there can be added as acid binding agents in known manner for the process of the invention aqueous solutions of inorganic bases, thus oxides, hydroxides, carbonates and bicarbonates of alkali and alkaline earth metals, e.g. sodium hydroxide, potassium hydroxide, calcium hydroxide, barium hydroxide, calcium oxide, barium oxide, sodium oxide, sodium carbonate, potassium carbonate, sodium bicarbonate and potassium bicarbonate. However, there are preferably used the hydroxides, particularly alkali hydroxides. They are preferably used in the form of aqueous solutions which contain the acceptor in concentrations of 10 to 50 weight %, particularly 20 to 40 weight %, preferably 20 to 30 weight %. For the synthesis step these acid acceptors are added in an amount of 0.96 to 1.02, preferably 0.98 to 1.02, equivalents per mole of cyanuric chloride, especially at the end of the reaction, i.e. in the production of 2-alkylamino-4,6-dichloro-s-triazines after the first synthesis step, or in the production of 2,4-di(alkylamino)-6-chloro-s-triazines after the second synthesis step, there should be present no stoichiometric excess.

In carrying out the process of the invention generally, the procedure is to dissolve or suspend the cyanuric chloride in the solvent mixture and then react these solutions or suspensions successively with the same or different amines first to 2-alkylamino-4,6-dichloro-s-triazines and then to 2,4-di(alkylamino)-6-chloro-s-triazines wherein if desired one or both alkyl groups can have substituents thereon. Since the reaction, therefore, takes place in two parts steps, the process of the invention is also very advantageously suited for the production of 2-alkylamino-4,6-dichloro-s-triazines if the reaction is broken off after the first step.

As amines for the reaction of the cyanuric chloride according to the invention there can be used in the first synthesis step, i.e. at least to the formation of the 2- alkylamino-4,6-dichloro-s-triazines (or substituted 2-alkylamino-4,6-dichloro-s-triazine) 1-cyanoalkylamine-1 such as α-aminoisobutyronitrile (1-cyano-1-methylethylamine-1), 1-cyano-1-methyl-propylamine, 1-cyano-1,2-dimethylpropylamine, 1-cyano-1-aminocyclohexane, 1-cyano-1-aminocyclopentane, 1-cyano-1-methylmethallylamine, 1-cyano-ethylamine-1, cyanomethylamine, 1-cyano-2-methylpropylamine, 1-cyano-methylthiopropylamine-1, or any of the other cyanoamines described as being useful in the production of halogenotriazines in German Pat. No. 1,670,520 and Schwarze U.S. Pat. No. 3,505,325 as well as simple and otherwise substituted alkylamines such as methylamine, dimethylamine, ethylamine, cyclohexylamine, di-n-butylamine, methyl ethyl amine, n-propylamine, isopropyl amine, cyclopropyl amine, t-butyl amine, ethyleneimine, diethylamine, n-hexyl amine, n-butyl amine, 3-methoxypropylamine, 2-methylmercaptoethylamine, ethanolamine, allyl amine, 3-ethoxypropylamine, 3-isopropoxypropylamine. If the cyanuric chloride is reacted to form 2-alkylamino-4,6-dichloro-s-triazines or to 2,4-di(alkylamino)-6-chloro-s-triazines with different alkylamino substituents in the 4 or 6-position, of the named amines the 1-cyanoalkylamines are preferred. It is particularly advantageous to employ α-aminoiso-butyronitrile for introduction of the first amine substituent into the triazine system. As amines for further reaction of the 2-alkylamino-4,6-dichloro-s-triazine into the corresponding 2,4-di(alkylamino)-6-chloro-s-triazine, there are usually employed simple primary and secondary amines such as methyl amine, dimethyl amine, ethyl amine, diethyl amine, n-propyl amine, isopropyl amine, di(isopropyl) amine, n-butyl amine, sec-butyl amine, di-n-butyl amine, t-butyl amine, n-hexyl amine, methyl propyl amine, cyclopropyl amine, cyclohexyl amine or diethyl amine. Ethyl amine and cyclopropyl amine are preferred, especially preferred being ethyl amine.

The process of the invention can be used, for example, to make any of the 2-amino-4,6-dichloro-s-triazines or 2,4-diamino-6-chloro-s-triazines disclosed in Schwarze U.S. Pat. No. 3,505,325, Ferguson U.S. Pat. No. 3,590,040, Petree U.S. Pat. No. 3,681,337, Saul U.S. Pat. No. 3,681,335, Saul German OG 1,670,042, Tandom German OG 1,964,619 or Hechenbleikner U.S. Pat. No. 2,476,546 starting from cyanuric chloride and the amines set forth in these United States patents and German Offenlegungsschrifts. The amine is added in the reaction of the invention in molar amounts, based on the cyanuric chloride employed; a slight amine excess, maximal 5%, preferably maximal 3% is permitted for the first reaction step, especially if a cyanoalkylamine is used as the amine. Such an excess is also permissible in the second reaction step, independent of the type of amine used. Less than molar amounts of amine per mole of cyanuric chloride employed always lead to a reduction in yield and reduction in purity of the product, and therefore desirably are avoided.

Thereby the amine can be used both in pure form and also in the form of a solution in an inert solvent, preferably in such which should be already present in the reaction as the components of the hydrocarbon-ketone system or, in the case the amine is not a cyanoalkylamine, also water.

The cyanoalkylamines, however, can also be added in the form of their equilibrium mixture of ketone cyanohydrin and ammonia dissolved in a stoichiometrical excess of ketone as is described in German Offenlegungsschrift 2,416,930 (the entire disclosure of which is hereby incorporated by reference and relied upon). The relatively small amount of water set free in establishing the equilibrium of ketone cyanohydrin and ammonia is not disturbing if an excess of ketone is present.

The dosing of the amine or amine solution should take place in such manner that the solvation and reaction enthalpy set free thereby cannot cause any increase in the temperature of the reaction mixture beyond the temperature limit for the process of the invention. In a given case the amine addition must take place correspondingly slower and/or with sufficient cooling. However, it should be understood that there can be used the solvation and reaction enthalpy in the amine addition partially or completely to establish the corresponding reaction temperature. Particularly this is possible at the beginning of the second synthesis step in the synthesis of 2,4-di(alkylamino)-6-chloro-s-triazines, i.e. at the addition of the second amine.

According to this process it is possible to obtain the 2-alkylamino-4,6-dichloro-s-triazine and especially the 2,4-di(alkylamino)-6-chloro-s-triazine particularly the 2-(1-cyano-1-methylethylamino)-4-ethylamino-6-chloro-s-triazine in yields of at least 97% of theory, at a purity of at least 97%. Using the preferred or especially preferred named mode of action there can even be attained yields of over 99% of theory at a product purity of over 98% or 99%. The products obtainable directly according to this process after the usual working up contain less than 0.7 weight % of unreacted cyanuric chloride and/or its hydrolysis products. In the synthesis of 2,4-di(alkylamino)-6-chloro-s-triazines, including those of the type of 2-(1-cyanoalkylamino)-4-alkylamino-6-chlorotriazines, these contain less than 0.3 weight % of the corresponding 2-alkylamino-4,6-dichloro or 2-(1-cyanoalkylamino)-4,6-dichloro-s-triazine) less than 1.0 weight % of 2,4-bis-alkylamino-6-chloro-s-triazine and less than 1.0 weight % of 2-(1-cyanoalkylamino)-4-amino-6-chloro-s-triazine. The latter can arise in a side reaction by reaction with ammonia of the 2-(1-cyanoalkylamino)-4,6-dichloro-s-triazine formed as an intermediate product, the ammonia coming from the hydrolytic back splitting of the cyanoalkylamine. This purity is shown by the product in the industrial plant without the necessity of including the further, previously necessary, purification operations such as washing, recrystallization, etc. Certain environmental problems caused by side reactions or the by-products formed thereby are eliminated by the new process.

As reaction products according to the process of the invention there is obtained a two or three phased mixture according to the starting concentration chosen for the cyanuric chloride and according to the type, i.e. the solubility, of the aminochlorotriazine produced, wherein the third phase is the solid. The customary working up methods used also adjusted according to these phase properties. For example, there is formed in the production of 2-(1'-cyano-1'-methylethylamino)-4-ethylamino-6-chloro-s-triazine, in case of starting with an about 10 weight % cyanuric chloride solution in toluene-acetone mixture, at temperatures above about 40° C. clear, 2-phased solutions which can be easily separated into a lower, aqueous-acetonic chloride containing phase and an upper, toluene-acetonic product containing phase. According to a preferred method of working up the product can be obtained therefrom directly in the stated purity and yield through evaporation of the solvent, for example by distillation, or after an in a given case connected distillative concentration by spray or drum drying.

A further suitable method is to substantially precipitate the product from the "upper" phase by partial evaporation of the solvent by concentration, for example, to a solid concentration of about 50 weight %, and then to separate off the main portion through customary solid separation processes such as centrifuging or filtration, while the mother liquor is recycled for concentration. The thus obtained, still solvent-wet product can be subsequently further dried through customary processes such as flow drying, fluidized bed drying, tray drying or simply in a drying chest. In an analogous manner these methods also can be used with the 3-phased reaction mixtures formed according to the process of the invention with solids separation before and/or after concentration after separation of the predominant aqueous phase.

However, it is also possible to precipitate a portion of the product by strong dilution of the reaction mixture with water, the thus precipitated solids and first then working up the remaining "organic" phase by evaporation of the solvent. To be sure in this variant of working up there is the danger of a reduction in yield through a certain solubility of the product in the ketone containing water. Precisely this effect plays a not inconsiderable disadvantageous part in the conventional process in which the end product still must be washed to produce sufficient product purity.

The 2,4-di(alkylamino)-6-chloro-s-triazines which can be produced according to the process of the invention correspond to general formula I

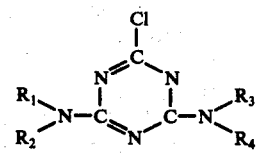

The symbols $R_1$ to $R_4$ in this formula have the following significance wherein by "lower alkyl group" is meant such having 1 to 6 carbon atoms. Preferably the alkyl groups have 1 to 4 carbon atoms.

$R_1$ and $R_2$ are the same or different and are straight or branch chain lower alkyl, alkenyl, cycloalkyl or methylcyclopropyl and, in a given case, can be substituted by —OH, —OR$_5$, —SR$_5$, —CN or halogen, e.g. chlorine, bromine or fluorine, where R$_5$ is a lower alkyl group. Preferably one of $R_1$ and $R_2$ is ethyl or cyclopropyl and preferably either $R_1$ or $R_2$ is hydrogen.

$R_3$ and $R_4$ can have the same meaning as $R_1$ and $R_2$. However, preferably $R_3$ is hydrogen and $R_4$ is the group

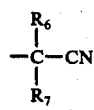

in which $R_6$ and $R_7$ are the same or different and are straight or branched alkyl or alkenyl groups with 1 to 8 carbon atoms which also can be closed to a 5 to 7-membered ring or can be a cycloalkyl group, preferably methyl, methylcyclopropyl or cyclopropyl, especially methyl and wherein either $R_6$ or $R_7$ can be hydrogen.

The process of the invention is particularly suitable for the production of compositions in which $R_3$ signifies a hydrogen atom and $R_4$ stands for the grouping

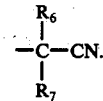

Again inside this group there is particularly preferred the production of 2-(1'-cyano-1'-methylethylamino)-4-ethylamino-6-chloro-s-triazine. In general formula I instead of

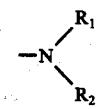

there can be a chlorine atom.

The amines which can be used in the invention correspond to general formulae II and III

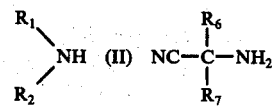

in which the symbols $R_1$ to $R_7$ have the meanings given in connection with formula I. The production is known for example from Schwarze German Pat. No. 1,670,578 and related Schwarze U.S. Pat. No. 3,505,325. As a rule there is first introduced the amine of general formula III and then the amine of general formula II.

The compounds obtained according to the process exhibit a biological activity. They particularly have herbicidal activity and also in part are suitable as intermediate products for the production of other active materials, particularly herbicide. By substitution of the residual chlorine atom in these compounds by mercapto, alkoxy, or alkylamino groups there are producible in particularly high yield and purity further industrially valuable products, for example, herbicides, rubber auxiliary agents, etc.

The following comparison and illustrative examples serve to further explain the invention.

An additional explanation of the process of the invention is given in the block diagram of FIG. 5.

Unless otherwise indicated, all parts and percentages are by weight.

EXAMPLE 1

There were placed in a 2 liter, fife necked flask equipped with a mechanical stirrer, reflux condenser, thermometer, glass electrode ( = single rod — measuring cell of the firm Schott and Gen., Jena, Type H, Zero point pH = 7, platinum diaphragm, calibrated in pure aqueous buffer solutions: pH = 7 (phosphate) and pH = 9 (boric acid — sodium hydroxide — KCl)), dropping in measurer and cooling bath a 10 weight % soltuion of 92.2 grams (0.5 mole) of cyanuric chloride in 829.8 grams of a mixture consisting of 70 weight % toluene and 30 weight % acetone (650.9 grams toluene and 278.9 grams acetone). The solution was cooled to 10° C. with stirring, then inside 20 minutes there were dropped in 44.6 grams of 98% (0.52 mole) of α-aminoisobutyronitrile. Then there were added 15 ml of water and there was begun the dropping in of 25 weight %, aqueous NaOH. The NaOH addition took place continuously, namely so that the following pH-time-progress was observed:

at the beginning of the NaOH addition: pH = 3.5

26 minutes after beginning of the NaOh addition: pH = 5.5

51 minutes after the beginning of the NaOH addition, addition of a further 140 ml of water and pH adjustment through regulating the NaOH addition speed to pH = 6.5

77 minutes after beginning of the NaOH addition: pH = 7.0

103 minutes after beginning of the NaOH addition: pH = 7.5

129 minutes after beginning of the NaOH addition, the temperature of the reaction mixture was increased to 35° C. and through regulation of the speed of adding NaOH a pH of 7.6 established, 154 minutes after beginning the NaOH addition: pH = 7.7

180 minutes after beginning the NaOH addition: pH = 7.7

In all there were added 79 grams of 25% NaOH. After that there were dropped in inside a further 20 minutes 57.1 grams of a 50 weight %, aqueous solution of cyclopropyl amine and then the reaction mixture warmed to 50° C. After reaching this temperature (after 15 minutes) there was dosed in furhter 25 weight % NaOH, namely again continuously, according to the following pH-time-progress at the beginning of the second NaOH addition: pH = 8.5

17 minutes after beginning the second NaOH addition: pH = 9.5

34 minutes after beginning the second NaOH addition: pH = 10.5

51 minutes after beginning the second NaOH addition: pH = 10.5

69 minutes after beginning the second NaOH addition: pH = 10.5

86 minutes after beginning the second NaOH addition: pH = 10.5

103 minutes after beginning the second NaOH addition: pH = 10.5

120 minutes after beginning the second NaOH addition: pH = 10.5

In all there were added 81 grams of NaOH (25%) in the second NaOH addition.

The reaction mixture obtained was diluted with 200 ml of acetone and thereupon subsequently a phase separation undertaken at 45° C. The aqueous phase was rejected; the organic phase together with the portions cyrstallized thereout evaporated to dryness in a vacuum and subsequently the residue dried in a vacuum at 60° C. until constant weight. There were obtained 126.1 grams of product which according to analysis consisted of 2-(1'-cyano-1'-methylethylamino)-4-cyclopropylamino-6-chloro-s-triazine) correspondingly 99.6% of the theoretical pure yield.

EXAMPLE 2

In a continuously operating apparatus to a stream of a 10 weight % solution of cyanuric chloride in a mixture consisting of 65 weight % toluene and 35 weight % acetone there were continuously fed 1.02 mole per mole of cyanuric chloride α-aminoisobutyronitrile. The mixture was held to a temperature of about +10° C. through a cooling zone and immediately after its formation, i.e. after the place of supplying the α-aminoisobutyronitrile lead to a reactor cascade. The volume of the cascade consisting of 4 reactors was so regulated that the average residence times therein were 20, then 10, then 70 and finally 175 minutes.

The temperatures of the reaction mixture in the individual reactors were held in order at 10, 10, 10 and 30° C. In the first reactor of the cascade besides there was continuously fed in water, namely at such a velocity that for a throughput velocity of 1 mole of triazine per hour about 27 grams of water per hour were fed in. Besides by the continuous addition of a 25 weight % aqueous solution of NaOH in the first reactor of the case there was maintained a pH of 4.6, (Measurement was with glass electrodes — single rod — measuring cell as described in example 1). There was likewise added to the product in the second reactor of the cascade water and again a 25 weight % aqueous solution of NaOH, namely the addition of water per 1 mole of triazine throughput per hour was at a velocity of 240 grams per hour; the NaOH addition was such that a constant pH = 5.0 was maintained. Also in the third and fourth reactors of the cascade there took place pH controlling, continuous addition of NaOH (25%, aqueous solution) namely so that this was established a pH = 6.0 in the third reactor of the cascade and a pH = 7.8 in the fourth reactor of the cascade. The reaction mixture leaving the fourth reactor of the cascade was mixed in a mixing nozzle with 50 weight % aqueous ethyl amine, namely at a veocity ratio of 1 mole per hour of ethyl amine per 1 mole per hour throughout of triazine. The reaction mixture was brought to a temperature of 50° C. by using the heat of mixing the two components and slight subsequent heating and immediately brought into a second reactor cascade, again consisting of four reactors. In the first reactor of this second cascade the pH was held at 7.1 by again continuous feeding, pH controlling 25% NaOH solution; in the second reactor of this second cascade through further feeding of 25% NaOH solution a pH = 7.6 was maintained; in the third reactor of this second cascade likewise through feeding 25% NaOH solution a pH of 8.7 was maintained and in the fourth (last) reactor of this second cascade a pH of 10.4 was maintained (again established by continuous addition of 25% NaOH) solution. The volumes of the individual reactors of the cascade were so regulated that the average residence time of the continuous stream of product corresponded to about 20, then 10, then 35, then 175 minutes. All reactors of the first and also of the second cascade were provided with a highly effective stirring system so that a demixing of the reaction mixture contained therein was impossible and homogeneous suspensions or solutions flowed from one reactor into the next. The reaction mixture leaving the last (fourth) reactor of the second cascade was led to an automatic phase separator from which the upper phase was continuously separated by way of a difference in density control and led to a drying aggregate (for solvent evaporation). There was obtained therefrom a continuous accumulation of at least 98.5 weight % of 2-(1'-cyano-1'-methylethylamino)-4-ethylamino-6-chloro-s-triazine in a yield on the average of about 99% of theory based on the cyanuric chloride added per hour at the beginning of the reaction. The triazones 2-(1'-cyano-1'-methylethylamino)-4,6-dichloro-s-triazine and 2,4-diethylamino-6-chloro-s-triazine were no longer detectible in the product by thin layer chromatography. The waste water resulting from the phase separator after distillative separation of the acetone contained therein contained practically only sodium chloride and traces of cynuric acid.

EXAMPLE 3

In a continuously operating apparatus to a stream of a 12 weight % suspension of cyanuric chloride in toluene there was continuously fed a stream coming from a mixing jet in which were fed in continuously 1.02 mole acetone-cyanohydrin and 1.02 mole liquid ammonia per mole cyanuric chloride. The mixture, identical with an approximately 9 weight % solution of cyanuric chloride in a solvent-mixture consisting of 27,85 weight % acetone and 72,15 weight % toluene mixed with 1.02 mole α-aminoisobutyronitrile and 1.02 mole water per mole cyanuric chlorde was held to a temperature of about +10° C. trough a heat-exchanger zone and immediately after its formation lead to a reactor cascade. The volume of the cascade consisting of 4 reactors was so regulated that the average residence times therein were 20, then 10, then 70 and finally 175 minutes.

The temperatures of the reaction mixture in the individual reactors were held in order at 10°, 10°, 10° and 30° C. In the first reactor of the cascade besides there was continuously fed in water, namely at such a velocity that for a throughput velocity of 1 mole of triazine per hour about 9 grams of water per hour were fed in. Besides by the continuous addition of a 25 weight % aqueous solution of NaOH in the first reactor of the case there was maintained a pH of 4.6, (Measurement was with glass electrodes — single rod — measuring cell as described in example 1). There was likewise added to the product in the second reactor of the cascade water and again a 25 weight % aqueous solution of NaOH, namely the addition of water per 1 mole of triazine throughput per hour was at a velocity of 240 grams per hour; the NaOH addition was such that a constant pH = 5.0 was maintained. Also in the third and fourth reactors of the cascade there took place pH controlling, continuous addition of NaOH (25%, aqueous solution) namely so that this was established a pH = 6.0 in the third reactor of the cascade and a pH = 7.8 in the fourth reactor of the cascade. The reaction mixture leaving the fourth reactor of the cascade was mixed in a mixing nozzle with 50 weight % aqueous ethyl amine, namely at a velocity ratio of 1 mole per hour of ethyl amine per 1 mole per hour throughput of triazine. The reaction mixture was brought to a temperature of 50° C by using the heat of mixing of the two components and slight subsequent heating and immediately brought into a second reactor cascade, again consisting of four reactors. In the first reactor of this second cascade the pH was held at 7.1 by again continuous feeding, pH controlling 25% NaOH-solution; in the second reactor of this second cascade through further feeding of 25% NaOH-solution a pH = 7.6 was maintained; in the third reactor of this second cascade likewise trough feeding 25% NaOH-solution pH of 8.7 was maintained and in the fourth (last) reactor of this second cascade a pH of 10.4 was maintained (again established by continuous addition of 25% NaOH-solution). The volumes of the individual reactors of the cascade were so regulated that the average residence time of the continuous stream of product corresponded to about 20, then 10, then 35, then 175 minutes. All reactors of the first and also of the second cascade were provided with a highly effective stirring system so that a demixing of the reaction mixture contained therein was impossible and homogeneous suspensions or solutions flowed from one reactor into the next. The reaction mixture leaving the last (fourth) reactor of the second cascade was led to an automatic phase separator from which the upper phase was continuously separated by way of a difference in density control and led to a drying aggregate (for solvent evaporation). There was obtained therefrom a continuous accumulation of at least 98.4 weight % of 2-(1'-cyano-1'-methylethylamino)-4-ethylamino-6-chloro-s-triazine in a yield on the average of about 99% of theory based on the cyanuric chloride added per hour at the beginning of the reaction. The triazines 2-(1'-cyano-1'-methylethylamino)-4,6-dichloro-s-triazine and 2,4-diethylamino-6-chloro-s-triazine were no longer detectible in the product by thin layer chromatography. The waste water resulting from the phase separator after distillative separation of the acetone contained therein contained practically only sodium chloride and traces of cyanuric acid.

In the claims, unless otherwise stated, the first amine and the second amine can be the same.

The process can comprise, consist essentially of, or consist of the steps set forth using the materials set forth.

We claim:

1. A process for the successive substitution of two chlorine atoms of cyanuric chloride comprising reacting the cyanuric chloride with two amines in the presence of an acid acceptor and an organic solvent to produce a triazine of the formula

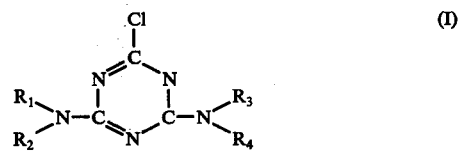

where $R_1$ and $R_2$ are lower alkyl, lower alkenyl, cyclo lower alkyl or methylcyclopropyl or such groups substituted by —OH, —OR$_5$, —SR$_5$ or CN where $R_5$ is lower alkyl, with the proviso that one of $R_1$ and $R_2$ can be hydrogen, and $R_3$ is as defined for $R_1$ or

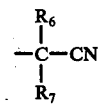

and $R_4$ is

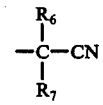

wherein $R_6$ and $R_7$ are alkyl or alkenyl of 1 to 8 carbon atoms, or together with the adjoining carbon atom form a 5 to 7 membered cycloalkyl ring or are cycloalkyl with the proviso that one of $R_6$ and $R_7$ can be hydrogen, said process comprising adding 1.00 to 1.05 mole of a first amine of the formula

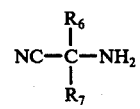

to a 4.5 to 50 weight % suspension or solution of cyanuric chloride in a mixture of 65 to 85 weight % of a hydrocarbon selected from the group consisting of benzene, toluene, xylene, ethylbenzene, aliphatic hydrocarbons having 5 to 10 carbon atoms, cycloaliphatic hydrocarbons having 5 to 10 carbon atoms and mixtures of such hydrocarbons and 35 to 15 weight % of a ketone having 3 to 8 carbon atoms, maintaining the temperature between about 0° and about 20° C., continuously regulating the pH value of the reaction mixture obtained in accordance with the reaction time by adding alkali that the relationship of pH to reaction time is in the area bonded by ABCD of FIG. 1 of the drawings beginning with the (reaction)time $t$(step 1) = 0 and containing until a position is reached in the area bounded by BCEF and after reaching a pH of 7.0 maintaining the temperature at about 10° to about 60° C. and after attaining said pH of 7.0 and after there has been added 0.96 ro 1.05 equivalents of alkali per mole of cyanuric chloride adding an at least equimolar amount of a different amine of the formula

per mole of cyanuric chloride and continuously adjusting the pH value of the reaction mixture according to the reaction time by addition of alkali that the relationship of pH to reaction time is in the area bounded by GHIJ of FIG. 3 beginning with the (reaction)time $t$(step 2) = 0 until a position is reached in the area bounded by HIKL while maintaining a temperature of 40° to 70° C. and thereafter recovering the triazine product formed, and wherein $t_1$ is 4 to 10 hours and $t_2$ is 2 to 8 hours and further wherein the line BC corresponds to the equation pH = $-(12.6/t_1)$ + 14.35 and the line HI corresponds the the equation pH = $-(24.857/t_2)$ + 23.9285.

2. A process according to claim 1 wherein the first amine is a cyanoalkylamine and the second amine is an alkylamine having 1 to 4 carbon atoms, cyclopropylamine or methyl cyclopropylamine.

3. A process according to claim 2 wherein the cyanoalkylamine is α-aminoisobutyronitrile.

4. A process according to claim 3 wherein the second amine is ethyl amine.

5. A process according to claim 3 wherein the second amine is cyclopropylamine.

6. A process according to claim 1 wherein $R_1$ and $R_3$ are both hydrogen.

7. A process according to claim 6 wherein $R_2$ is lower alkyl, lower alkenyl, cyclolower alkyl or methylcyclopropyl and wherein one of $R_6$ and $R_7$ is alkyl or alkenyl having 1 to 8 carbon atoms and the other is hydrogen, alkyl or alkenyl having 1 to 8 carbon atoms and wherein $R_6$ and $R_7$ together with the adjoining carbon atom may form a 5 to 7 member cycloalkyl ring.

8. A process according to claim 1 wherein there is added 1.00 to 1.02 mole of the second amine per mole of the cyanuric chloride.

9. A process according to claim 8 wherein there is employed 1.00 to 1.03 moles of the first amine and the temperature is initially regulated to about 10° to 18° C. and the temperature in the first step after reaching a pH of 7.2 is maintained at 25° to 40° C. after there has been added 0.98 to 1.02 equivalents of alkali per mole of cyanuric chloride and the temperature in the second step is kept at 45° to 55° C.

10. A process according to claim 1 wherein after addition of the first amine the temperature is maintained between about 0° and about 20° C. in steps (1a), (1b) and (1c) while adding alkali under the following schedule of pH and time:

1a. pH of 3.5 to 5 with an average residence time of 3 to 43 minutes;
1b. pH of 4.5 to 6.25 with an average residence time of 0 to 56 minutes;
1c. pH of 5.5 to 7.0 with an average residence time of 17 to 189 minutes, and
1d. pH of 7.0 to 8.0 with an average residence time of 30 to 493 minutes at a temperature of 10 to 50° C.

11. A process according to claim 10 wherein after addition of the second amine the temperature is maintained between about 40 and about 70° C. while adding alkali under the following schedule of pH and time:

2a. pH of 6.5 to 8.0 with an average residence time of 2 to 60 minutes,
2b. pH of 7.5 to 9.0 with an average residence time of 0 to 92 minutes,
2c. pH of 8.0 to 10.0 with an average residence time of 0 to 172 minutes, and
2d. pH of 10 to 11.25 with an average residence time of 15 to 408 minutes.

12. A process according to claim 11 wherein the first amine is a cyanoalkylamine and is formed in situ by adding a mixture of a ketone cyanohydrin and ammonia dissolved in a stoichiometrical excess of ketone.

13. A process according to claim 11 wherein after addition of the first amine the temperature is maintained between about 10 and about 10° C. in steps (1a), (1b) and (1c) while adding alkali under the following schedule of pH and time:

1a. pH of 4.25 to 4.75 with an average residence time of 9 to 21 minutes,
1b. pH of 5.0 to 5.5 with an average residence time of 3 to 18 minutes,
1c. pH of 5.75 to 6.25 with an average residence time of 51 to 93 minutes, and
1d. pH of 7.25 to 7.90 with an average residence time of 135 to 330 minutes while maintaining a temperature of 15° to 35° C., and wherein after addition of the second amine the temperature is maintained between about 45° and about 55° C. while adding alkali under the following schedule of pH and time:

2a. pH of 6.75 to 7.25 with an average residence time of 10 to 30 minutes,
2b. pH of 7.5 to 8.0 with an average residence time of 0 to 36 minutes,
2c. pH of 8.25 to 8.75 with an average residence time of 9 to 66 minutes, and
2d. pH of 10.25 to 10.75 with an average residence time of 135 to 306 minutes.

14. A process according to claim 13 wherein the first amine is a cyanoalkylamine and the second amine is an alkylamine having 1 to 4 carbon atoms, cyclopropylamine or methyl cyclopropylamine.

15. A process according to claim 14 wherein the cyanoalkylamine is α-aminoisobutyronitrile.

16. A process according to claim 15 wherein the second amine is ethyl amine or cyclopropylamine.

17. A process according to claim 11 wherein the first amine is a cyanoalkyl amine and the second amine is an alkyl amine having 1 to 6 carbon atoms, cyclopropylamine or methyl cyclopropylamine.

18. A process according to claim 17 wherein the cyanoalkylamine is α-aminoisobutyronitrile.

19. A process according to claim 1 carried out continuously employing a cascade of reactors dimensioned so as to provide the stated average residence times.

20. The process of claim 1 wherein the hydrocarbon solvent is benzene, toluene, xylene, ethyl benzene or a mixture thereof and the ketone solvent is acetone.

21. The process of claim 1 wherein the hydrocarbon solvent is toluene.

* * * * *